United States Patent
Albert et al.

[11] Patent Number: 5,951,291
[45] Date of Patent: Sep. 14, 1999

[54] COSMETIC ACCESSORY DEVICE FOR TEETH

[75] Inventors: Nancy M. Albert, Grovetown, Ga.; Daniel Cho, New Milford, Conn.

[73] Assignee: Bukk, Inc., Grovetown, Ga.

[21] Appl. No.: 08/912,183

[22] Filed: Aug. 15, 1997

[51] Int. Cl.$^6$ ........................................... A61C 5/00
[52] U.S. Cl. ........................... 433/215; 433/26; 433/167; 433/196
[58] Field of Search ................. 433/2, 26, 167, 433/171, 196, 215; 472/70

[56] References Cited

U.S. PATENT DOCUMENTS

| | | | |
|---|---|---|---|
| 2,516,155 | 7/1950 | Slack, Jr. | 433/214 |
| 3,987,546 | 10/1976 | Trampe | 433/213 |
| 4,300,886 | 11/1981 | Siiling et al. | 433/171 |
| 4,370,133 | 1/1983 | Stempel | 433/171 |
| 4,457,713 | 7/1984 | Schneider | 433/171 |
| 4,515,913 | 5/1985 | Pellico | 523/109 |
| 4,521,193 | 6/1985 | Cialone | 433/199 |
| 4,527,975 | 7/1985 | Ghafari et al. | 433/8 |
| 4,529,777 | 7/1985 | Daidone | 525/193 |
| 4,559,013 | 12/1985 | Amstutz et al. | 433/8 |
| 4,626,558 | 12/1986 | Pellico | 523/109 |
| 4,676,500 | 6/1987 | Fricano | 272/8 N |
| 4,978,298 | 12/1990 | Eliasz | 433/213 |
| 5,037,473 | 8/1991 | Antonucci et al | 106/35 |
| 5,083,770 | 1/1992 | Holland | 272/8 R |
| 5,324,198 | 6/1994 | Hazen | 433/171 |
| 5,430,074 | 7/1995 | Barnes et al. | 523/115 |
| 5,588,834 | 12/1996 | Resk et al. | 433/26 |

*Primary Examiner*—John J. Wilson
*Attorney, Agent, or Firm*—Maria Reichmanis

[57] ABSTRACT

A cosmetic accessory device for teeth that simulates the appearance of an assemblage of teeth and gum. The device includes a gum portion and a tooth portion shaped and dimensioned to cover the user's upper or lower front teeth. The device is made of a nontoxic, nonirritating, tasteless, odorless, resilient, easily cleaned and chemically stable material that does not stick to natural teeth, gums, or most dental work. In use, the device is held in place by custom-fitted inner projections that match the spaces between the user's own front teeth and (optionally) a shelf extending just across the front teeth. Unlike typical conventional novelty dental devices, the natural teeth and gums are not completely covered, so the device is comfortable to wear and does not interfere with natural speech or bite closure.

20 Claims, 3 Drawing Sheets

COSMETIC ACCESSORY DEVICE FOR TEETH

BACKGROUND OF THE INVENTION

1. Field of the Invention

The present invention relates to cosmetic accessory devices. In particular, the present invention relates to a removable cosmetic accessory device that is worn to enhance the user's appearance, and a method and kit for making and fitting the device.

2. Discussion of Background

Present-day dentures are a far cry from the wood and ivory devices that were available in the eighteenth and nineteenth centuries. The widespread use of fixed and removable bridges, crowns, implants and cosmetic overlays, coupled with advances in orthodontics and the availability of new dental materials, have revolutionized dentistry. It is now possible to restore many teeth that only a generation ago would have been lost, or to replace missing teeth with a functional denture that so closely resembles natural teeth and gums that only the user knows he is wearing a prosthesis rather than "the real thing."

Many different types of dentures and dental devices are available, including removable prosthetic devices that replace missing teeth, permanent implants, crowns and bridges, temporary dentures and other devices intended for short-term wear, and novelty devices worn primarily for their entertainment value. Even temporary dentures can be both functional and realistic in appearance. For example, Cialone, in U.S. Pat. No. 4,521,193, describes a method and kit for making a temporary denture using a quick-cure acrylic composition.

A variety of materials are used for making dentures and denture liners, including thermally deformable acrylic polymers (Trampe, U.S. Pat. No. 3,987,713), methacrylate polymer compositions (Antonucci, et al., U.S. Pat. No. 5,037,473), polyacrylamide compositions (Pellico, U.S. Pat. No. 4,626,558 and U.S. Pat. No. 4,515,913), methyl methacrylate-based dental casting resin (Daidone, U.S. Pat. No. 4,529,777), ethyl methacrylate polymer mixed with alcohol and naphtha (Slack, Jr., U.S. Pat. No. 2,516,155). Eliasz incorporates filler particles (nylon or precured acrylic spheres or cylinders) of a predetermined, uniform diameter into a wax sheet used for making dental impressions (U.S. Pat. No. 4,978,298). Süling, et al. disclose polymethacrylate bead polymers ("dental beads") for making dentures (U.S. Pat. No. 4,300,886).

Typical dentures are fitted to surround the user's gums (Schneider, U.S. Pat. No. 4,457,713; Stempel, U.S. Pat. No. 4,370,133; Trampe, U.S. Pat. No. 3,987,546). However, unlike conventional full dentures that can only be fitted to an edentulous jaw, Hazen's removable denture covers the user's remaining natural teeth (U.S. Pat. No. 5,324,198).

Additional types of dental devices are used for entertainment, and are not intended to simulate natural teeth. These are generally worn for relatively short periods of time, and range from such classic disguise devices as "blacked-out" teeth, simulated cavities and "gold" teeth to vampire-like fangs and other theatrical accessories. People who follow certain fashion trends sometimes attempt to glue decorations such as metallic cutouts, and simulated precious stones to their natural teeth, with varying degrees of success. The adhesives used to attach these types of ornaments to the teeth may irritate sensitive oral tissues, leading to potentially serious health consequences (inflammation, infection, damage to the teeth and gums, and so forth).

Holland (U.S. Pat. No. 5,083,770) shows a device that includes fangs and a bladder with discharge ports. Users can compress the bladder with their tongues to discharge simulated blood from apertures near the tips of the fangs. Fricano (U.S. Pat. No. 4,676,500) shows fangs made of injection molded polyvinylchloride that can be retracted or extended by biting down on rollers held between the user's own teeth. All of these devices either surround the user's own teeth and gums, or have wires or other supports that obtrude into the user's mouth. Such devices are frequently difficult to fit, uncomfortable to wear, and interfere with the user's normal speech patterns.

In patent application Ser. No. 08/510,005, filed Aug. 1, 1995, Albert discloses a dental disguise device that simulates the appearance of an assemblage of teeth and gums. This entertainment device, which covers the user's upper front teeth and gums, is made of a nontoxic, chemically stable material that does not stick to natural teeth and gums, or indeed to most dental work. In use, the device is held in place by the springiness of the material and by inner projections that fit into the spaces between the user's own front teeth. No material extends around or behind the user's natural teeth and gums, thus, the device is relatively comfortable to wear and does not interfere with natural speech or bite closure. The device, which can be custom-fitted by the user, is made in several sizes to accommodate the range of upper jaw sizes found in adults.

Modern dentistry can accomplish seeming miracles for those patients who can afford to pay the price, but offers little for many others who would like to have better-looking teeth without the time, discomfort, and expense associated with extensive dental work. Despite the wide variety of restorative dental techniques and cosmetic dental devices available to consumers, there is no known dental device that is inexpensive, easy to fit and wear, and readily adaptable to both entertainment and cosmetic purposes. Fitting typical, presently-available devices requires a multi-step, iterative process which can be difficult for persons with limited manual dexterity. In addition, many consumers find it difficult or uncomfortable to make an impression of their own natural teeth for fitting purposes. The availability of a suitable cosmetic accessory that could be worn whenever the user wished to feel more confident about his or her appearance, and to appear more attractive.

There is a need for a dental accessory device made of nontoxic and nonirritating materials, that can simulate a variety of dental conditions, and that can be worn over the user's own upper front teeth and gums to enhance his or her appearance. Such a device could be worn whenever the user wished to enhance his or her appearance. It should be simple and easy to fit (preferably in a single size that can be fitted to all prospective users), comfortable to wear, difficult to detect, and allow the user to speak and drink normally.

SUMMARY OF THE INVENTION

According to its major aspects and broadly stated, the present invention is a removable cosmetic accessory device that simulates the appearance of an assemblage of teeth and gums. The device, which includes a gum portion and a tooth portion, is shaped and dimensioned to cover the user's front teeth and at least a portion of the gums. To enhance the user's appearance and thereby further self-esteem, the tooth portion is preferably shaped to resemble attractive natural teeth. However, if desired, the tooth portion may simulate the appearance of unsightly teeth to effect a convincing theatrical disguise. In a preferred embodiment of the invention, the device is in the form of a somewhat flexible shell that is custom-fitted to an individual user with a room-temperature-curable polymer material.

An important feature of the present invention is the method for custom-fitting the accessory device to an individual user. The device is fitted by coating at least part of its interior surface with a room-temperature-curable polymer material, then pressing it firmly onto the user's front teeth, with the coating engaging the teeth, until the material is at least partly cured (if desired, a thin ledge or shelf of the polymer material may be formed just across the cutting edges of the front teeth). The device is then removed from the user's mouth and trimmed of any excess material that might interfere with his or her comfort during wear. To accelerate final curing, the device may be soaked in hot water before trimming.

In a preferred embodiment of the invention, the fitted device is a thin, somewhat resilient and somewhat flexible shell with an approximately semi-circular cross-section. When properly positioned for wearing, its shape, together with the custom-fitted inner projections that protrude into the spaces between the user's upper front teeth and the ledge (if present), holds the device in place in the user's mouth. Unlike conventional dentures and dental accessories, a device according to the invention does not fully cover the user's natural teeth and gums, so it is comfortable to wear and does not interfere with natural speech or bite closure.

Another important feature of the present invention is the selection of materials used for making the device. The device is made of nontoxic, somewhat resilient, chemically stable materials that are tasteless, odorless, easily cleaned, and do not stick to natural teeth, gums, or most dental work (fillings, crowns, bondings, inlays, bridges, etc.). Preferably, the device is made of a workable, curable silicone composition (medical or food grade) with a tear strength or elongation of at least approximately 150% when cured. A wide range of materials are broadly suitable for use with the invention, ranging from approximately 1:1 ratio curing silicones to 100:1 ratio silicones; however, other materials with the requisite properties may also be suitable. For a secure fit, the tooth portion of the device is preferably made of a harder material than either the gum portion or the fitting material.

Another feature of the present invention is the tooth portion of the device, which not only serves to maintain the position of the device in use but is the most readily apparent to others. The tooth portion is dimensioned to cover the upper front teeth, preferably those teeth that are most visible when the wearer smiles (the incisors and canines, and preferably also the first premolars, i.e., the premolars immediately adjacent to the canines). As noted above, the tooth portion includes custom-fitted inner projections and, optionally, a ledge or shelf that maintain its position during normal wear but are generally concealed from view. Depending on the cosmetic appearance of the tooth portion, the device may be worn as an accessory to enhance the user's appearance and foster increased self-esteem, as an amusing disguise to entertain the user and others, as a theatrical accessory, or as a teaching tool to demonstrate the results of planned dental treatment.

The tooth portion is preferably shaped to simulate the appearance of natural teeth, preferably attractive teeth that help enhance the user's appearance and further increased self-confidence. If desired, the tooth portion may include fashionable decorations such as simulated gold crowns, metallic or precious stone insets, and like decorations. In this embodiment, the device is worn as an accessory, for example, as a cost-effective device for concealing unattractive teeth, to camouflage dental braces for a special occasion, or to show the projected results of recommended dental treatment (braces, crown and bridge work, implants, and so forth). Alternatively, the tooth portion of the device may be decorated to resemble unattractive teeth.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1A:
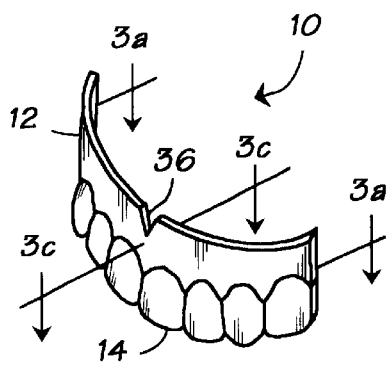
FIG. 1A is a perspective view of a dental accessory device according to a preferred embodiment of the present invention.

In the following detailed description, like reference numerals are intended to identify the same structural elements, portions or surfaces consistently throughout the several drawing figures, as such elements, portions or surfaces may be further described or explained by the entire written specification. As used in the following description, the terms "horizontal," "vertical," "left," "right," "up," "down," as well as adjectival and adverbial derivatives thereof (e.g., "horizontally," "rightwardly," "upwardly," etc.) refer to the relative orientation of the illustrated structure as the particular drawing figure faces the reader. Similarly, the terms "inwardly" and "outwardly" refer to the orientation of a surface of revolution relative to its axis.

Figure 1B:
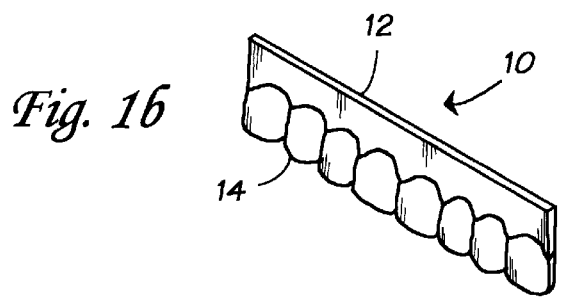
FIG. 1B is a perspective view of another dental accessory device according to the invention.

Referring now to FIG. 1A, there is shown a perspective view of a dental accessory device 10 according to a preferred embodiment of the present invention. Device 10, which is shaped to approximate the curvature of the average adult upper jaw, simulates the appearance of an assemblage of teeth and gums with a gum portion 12 and tooth portion 14. When fitted to an individual user and worn over his or her own upper front teeth and gum, accessory device 10 covers the teeth that are most visible when the user smiles. Preferably, device 10 is dimensioned to cover at least the six center front teeth (the upper incisors and canines); more preferably, at least eight center front teeth. Alternatively, device 10 may be approximately rectilinear (FIG. 1B). Device 10 as illustrated in FIGS. 1A and 1B is a maxillary or upper dental device; however, it will be appreciated that the following description is equally applicable to a mandibular dental device that covers the lower front teeth and gums.

Figure 2:
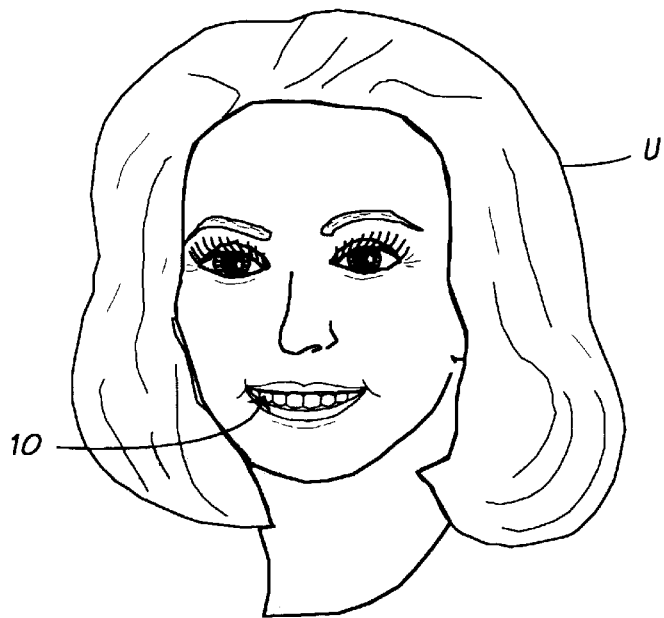
FIG. 2 shows the device of FIG. 1A worn by a user.

In accordance with a preferred embodiment of the present invention, tooth portion 14 of accessory device 10 is shaped to simulate attractive natural teeth (device 10 is shown worn by a user U in FIG. 2). While it is believed that most users prefer a device that resembles natural, unadorned teeth, device 10 may be embellished with fashionable decorations such as simulated gold crowns, gold insets or precious stone insets if desired. Alternatively, device 10 may include simulated cavities, fissures, sores, etc., such as those described in co-pending application Ser. No. 08/510,005. Thus, device 10 may be used as a cosmetic or therapeutic accessory to enhance the user's appearance and self-esteem, as an amusing disguise or theatrical accessory to give the user the appearance of teeth different from his or her own, as an educational tool to teach children the value of good dental hygiene and the consequences of poor hygiene, or as an accessory to illustrate the results of planned dental treatment.

Figure 3A:
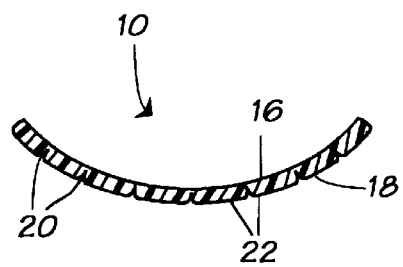
FIG. 3A is a cross-sectional view of the device of FIG. 1, taken through the lines 3A—3A of FIG. 1.

Before fitting, device 10 is a thin shell with an approximately smooth inner surface 16 and an outer surface 18 (FIG. 3A). Surface 18 preferably has a plurality of indentations 20 that delineate individual "teeth" 22. Gum portion 12 is colored to resemble natural gum tissue, by incorporating a suitable coloring agent into the material of gum portion 12, painting surface 18 of portion 12 after manufacture of device 10, or some other convenient technique. Similarly, tooth portion 14 is colored to resemble natural teeth.

After fitting to an individual user, accessory device 10 is a thin, arcuate shell (preferably no more than approximately 2–3 mm thick). The tooth portion of inner surface 16 is at least partly covered by a thin layer 30 of fitting material that forms projections 32 that fit into the interdental spaces between the user's teeth (FIG. 3B) and, optionally, an inwardly-projecting ledge or shelf 34 that help maintain the position of device 10 during wear.

Device 10 is made of any nontoxic, nonirritating, tasteless, odorless material (or combination of materials) that has sufficient structural and mechanical integrity to maintain its shape and secure the device in place during normal activities (speaking, laughing, drinking, and so forth). The material (or materials) is chemically stable and easy to clean, and somewhat flexible and resilient to facilitate fitting and minimize irritation to the user's mouth. In addition, the material does not stick to natural teeth, gums, or most dental work (fillings, inlays, crowns and bridges, bondings, etc.). To permit fitting device 10 to an individual user, the preferred material is firm at body temperature and lower temperatures. Suitable materials for device 10 include polyesters, silicones, alkyd resins and acrylic polymers having the foregoing properties, preferably of medical grade or food grade.

Preferably, device 10 is made of a room-temperature-curable material such as silicone, with an elongation (when cured) of at least approximately 150%, a durometer hardness of at least approximately 20 Shore A, and a viscosity of at least approximately 40,000 CPS at 72° F. (about 22° C.). More preferably, the material of tooth portion 14 has a greater hardness and a greater viscosity than the material of gum portion 12. As used herein, the terms "elongation" and "tear strength" refer to the force needed to initiate or to continue tearing a sheet or fabric. The terms "cure" or "vulcanization" refer to a chemical reaction of sulfur or other vulcanizing agent with rubber or plastic to cause cross-linking of the polymer chains; curing increases the strength and resilience of a polymer.

Fitting material 30 has an elongation or tear strength at least approximately equal to the elongation of tooth portion 14 and gum portion 12, preferably greater (at least approximately 200%). While portions 12, 14, and fitting material 30 may have similar hardnesses, material 30 is preferably harder, with a durometer rating of at least approximately 30 Shore A. As used herein, the term "hardness" refers to the resistance of a material to indentation, scratching, or abrasion. The "Shore hardness" of a material is found by measuring the height of rebound of a small drop hammer from the surface.

In addition, to help maintain the structural integrity and fit of device 10, fitting material 30 has a greater viscosity, or resistance to flow, than portions 12 and 14 (on the order of 400,000 CPS or higher at 72°0 F.). The preferred properties of these materials are summarized in Table I.

TABLE I

Preferred properties of materials suitable for manufacturing device 10

| | Gum Portion 12 | Tooth Portion 14 | Fitting Material 30 |
|---|---|---|---|
| Elongation | ≧150% | ≧150% | ≧150% |
| Durometer Hardness (Shore A) | 20–40 | 40–50 | 30–40 |
| Viscosity (CPS) | 40,000–60,000 | 50,000–80,000 | 400,000–600,000 |

While materials with the properties listed in Table I are preferred, materials having elongations, hardnesses and viscosities outside these ranges may also be suitable for the practice of the invention.

Suitable materials include the group of workable silicones which cure at approximately room temperature or thereabouts (i.e., about 72° F. or 22° C.). A wide range of such materials are broadly suitable for use with the invention, with base:catalyst ratios ranging from 1:100 or less to approximately 1:1. Such materials are well known in the art and need not be described in detail hereafter. The optimum materials for making and fitting device 10 are best selected by a modest amount of experimentation and observation by those of ordinary skill in the art. It will be obvious to those of ordinary skill that other materials which have the above-described properties may be employed in the practice of the invention.

The present invention is further illustrated in the following nonlimiting example.

EXAMPLE

A cosmetic accessory device according to the invention was made of materials having the following properties: portion 12 had an elongation of 150%, a durometer hardness of 30 Shore A, and a viscosity of approximately 50,000 CPS; portion 14 had an elongation of 150%, a hardness of 45 Shore A, and a viscosity of approximately 65,000 CPS.

The device, which was shaped and dimensioned for wearing over the user's upper front teeth, was molded in two stages (it will be understood that either of portions 12, 14 may be molded in the first stage of fabrication of device 10, with the other portion being molded in the second stage).

The resulting product was painted to resemble natural teeth, then fitted to a user. The fitting material (i.e., material 30) was a room-temperature-curable, 1:1 ratio silicone material that, when cured, had an elongation of approximately 200%, a hardness of 35 Shore A, and a viscosity of approximately 500,000 CPS. A satisfactory fit was achieved, with projections 32 and a shelf 34 that helped maintain the position of the device during use.

Device 10 may be manufactured by any suitable technique, including molding, stamping, casting, etc. The device is preferably made as a single unit, with portions 12 and 14 being painted or dyed to resemble natural gums and teeth, respectively. However, portions 12 and 14 could be manufactured separately of different-colored materials, then bonded together to form device 10. Suitable paints or dyes for use with device 10 are nontoxic and chemically stable.

It is known in the art that the range of individual variations in the size of the adult human mouth and teeth is relatively small. For example, the lateral spacing between the rear molars is approximately 2" (about 5 cm). Therefore, an accessory device according to the present invention can be made in a range of sizes to cover the expected range of variations commonly found in the adult human mouth (smaller sizes may be made for children, if desired). Preferably, however, the device is made in a single size that fits substantially all adults, and fitted in a manner to be described below.

Figure 4:
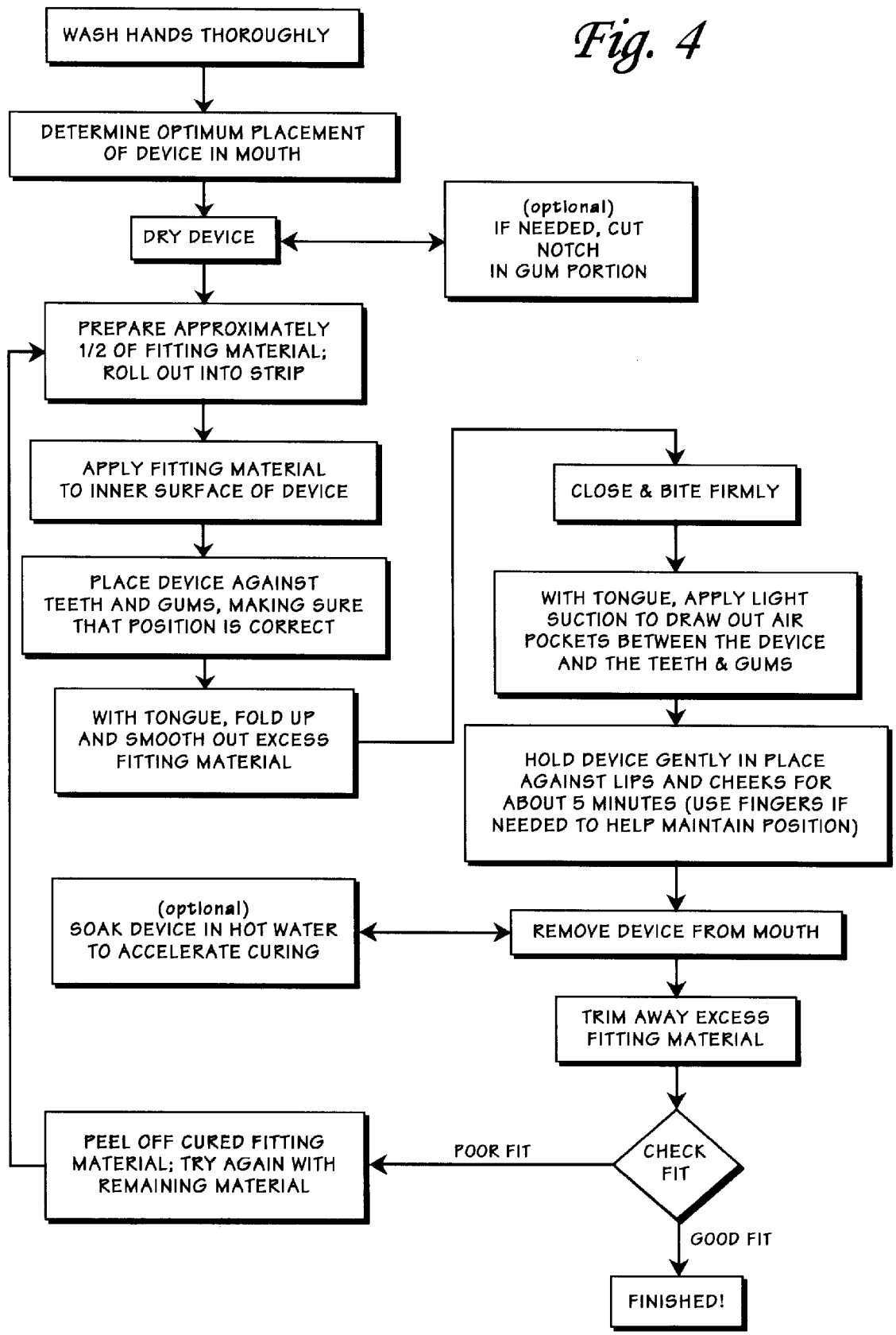
FIG. 4 is a flow chart illustrating a method for custom-fitting the device of FIG. 1 to a individual user.
Figure 5:
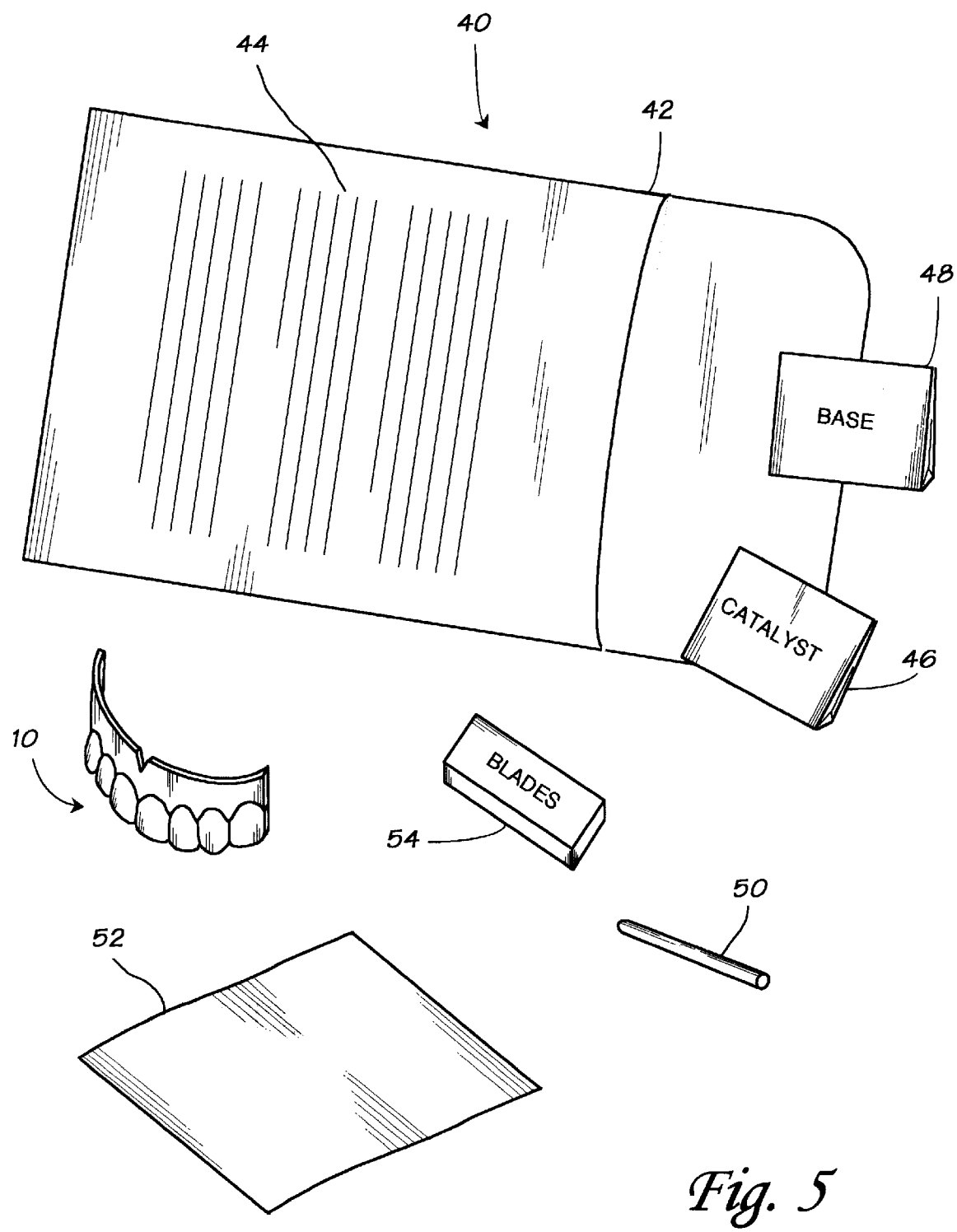
FIG. 5 shows a kit for custom-fitting the device of FIG. 1 to an individual user.

Referring now to FIG. 4, there is shown a method for fitting device 10 to an individual user. As shown in FIGS. 1A and 1B, device 10 is supplied in the form of a shell bearing the outlines of several front teeth (device 10 is shown as an accessory for the user's upper front teeth; however, it will be understood that device 10 may readily be shaped and dimensioned for covering the lower front teeth). The device may be supplied in kit form (see kit 40, FIG. 5), with a container 42, fitting instructions 44, a device 10, and envelopes 46, 48 that contain the two components (base and catalyst, respectively) of fitting material 30. Kit 40 may also include a stirrer 50, a sheet of wax paper 52 or similar material on which the user can mix material 30, and razor blades 54.

The user proceeds to custom-fit device 10 to his or her mouth as follows:

1. Wash hands thoroughly.
2. Determine the preferred placement of device 10 in the mouth: in front of a mirror, try several positions and select the most comfortable and attractive one. Remove device 10 from the mouth and dry the device.

If needed, cut a small notch 36 into gum portion 12 (FIG. 1A). Notch 36 accommodates the frenum (a small web of connective tissue that extends between the gum and the upper lip) that may otherwise, in some users, interfere with the proper placement of device 10. Device 36 may, of course, be supplied with a pre-cut notch 36, positioned generally as indicated in FIG. 1A.

3. Open envelopes 46, 48, and deposit approximately one half of the contents of each envelope onto a non-stick surface such as a sheet of wax paper.
4. Using the fingers (or a stirrer if desired), prepare fitting material 30 by mixing materials 46, 48 together until the mixture is uniform in color. Set aside envelopes 46, 48 with the remaining materials.
5. Roll out fitting material 30 into a strip and apply to the back of device 10, preferably covering substantially all of inner surface 16 of tooth portion 14. Make sure that material 30 is applied completely across the lower edge of device 10.
6. Using a mirror, firmly push device 10 straight into position against the upper front teeth and gums, with fitting material 30 on the inside (i.e., contacting the teeth and gums). Do not bite into fitting material 30. Push inner surface 16 of device 10 (covered with fitting material 30) against the teeth and gums, making sure that the device is properly positioned.
7. Using the tongue, gently fold up and smooth out excess fitting material 30. If desired, form a thin ledge 34 across the cutting edge of the teeth (see FIG. 3C).
8. Close bite firmly.
9. Using light suction, draw out any air pockets between device 10 and the teeth and gums. Hold device 10 gently in place (using the fingers if needed to help maintain the device in position) for approximately five (5) minutes, or until fitting material 30 is at least partly cured.
10. Remove device 10 from the mouth. Trim away any excess fitting material 30, including any which has escaped over the top of device 10 and any that impedes the natural bite. Retain some projections (i.e., projections 32, FIG. 3B), since these are necessary to hold device 10 in place during use.

Many polymers cure at a faster rate when heated. If fitting material 30 is this type of polymer, soak device 10 in hot water for a few minutes to accelerate curing of the material. Then, proceed to trim away excess fitting material.

11. Check the fit of device 10: If inner surface 16 bears a clear imprint of the surfaces of at least six teeth (see FIG. 3B), place the device into the mouth and test whether it fits comfortably. If yes, device 10 is finished and ready for use.

If inner surface 16 does not have a sufficiently clear imprint of the user's front teeth or does not fit comfortably, peel away fitting material 30, and use the remaining materials in envelopes 46, 48 to try again (most users achieve a good fit in their first attempt at custom-fitting device 10).

Device 10 is preferably furnished in a size that can readily be fitted to the vast majority of adults and, indeed, to many older children as well (as noted above, the dimensions of the average adult human mouth and teeth do not vary significantly). For users with somewhat smaller-than-average jaws, a portion of device 10 with one or more of the "teeth" may be cut off so as to help achieve a better fit. Alternatively, device 10 can be made in a range of sizes.

Tooth portion 14 is dimensioned to resemble typical, average or medium-sized teeth, as such teeth are generally considered to be more esthetically pleasing than noticeably large or small teeth. Tooth portion 14 and gum portion 12 are painted or colored in some way to resemble natural teeth and gums. As will be evident, the colors of portions 12, 14 may be selected to approximately conform to the average colors of healthy, attractive natural tissues. If desired, these colors may be selected to harmonize with the user's own coloring (skin tones, hair color, eye color).

As noted above, device 10 is made of materials that do not stick to natural teeth or most dental work. However, the device and/or fitting material 30 may mechanically surround or adhere to dental braces, exposed wires of partial dentures, and similar items when softened. When fitting device 10 to an individual who wears braces or other dental appliances with exposed wires, it is preferable to cover and round off the wires with removable wax before placing the device over the teeth. It will be evident to those skilled in the art that device 10—and other novelty dental devices—are best used only by those with reasonably good oral health (i.e., no sores, infections, unhealed extraction sites, etc.).

Figure 3B:
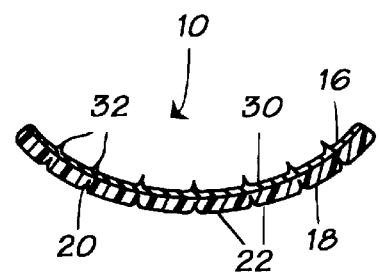
FIG. 3B is a cross-sectional view of the device of FIG. 3A, after the device has been custom-fitted to an individual user.
Figure 3C:
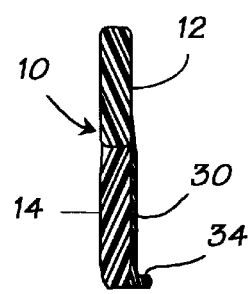
FIG. 3C is a cross-sectional view of the device of FIG. 3A after fitting, taken through the lines 3C—3C of FIG. 3A.

In use, a fitted accessory device 10 is worn engaging the upper front teeth so that projections 30 fit into the spaces between the user's natural teeth and shelf 34 (if present) is just under the teeth. As best seen in FIG. 3B, device 10 is approximately semi-circular in cross-section after fitting. Thus, custom-fitted projections 32 and shelf 34 hold device 10 in place in the user's mouth. Unlike conventional dental accessories, the natural teeth and gums are not fully covered, so device 10 is comfortable to wear and does not interfere substantially with natural speech or bite closure. The user is able to speak, laugh, open and close his mouth, and drink normally while wearing the device.

It will be apparent to those skilled in the art that many changes and substitutions can be made to the preferred embodiment herein described without departing from the spirit and scope of the present invention as defined by the appended claims.

What is claimed is:

1. A cosmetic accessory device, comprising:
   a first portion having an outer surface shaped to resemble an assemblage of front teeth, said first portion including a tooth portion made of a first somewhat resilient material and a gum portion made of a second somewhat resilient material; and
   a second portion adapted for attachment to an inner surface of said first portion and fitting said device to a user, said second portion made of a room-temperature-curable material, said first material being harder than said second material and said room-temperature-curable material.

2. The device as recited in claim 1, wherein said room-temperature-curable material is a silicone material.

3. The device as recited in claim 1, wherein said room-temperature-curable material is selected from the group consisting of medical grade and food grade silicone materials.

4. The device as recited in claim 1, wherein said first and second materials are selected from the group consisting of curable silicone materials.

5. The device as recited in claim 4, wherein said first material and said second material have elongations at least approximately equal to 150%, and wherein said room-temperature-curable material has an elongation at least approximately equal to 200%.

6. The device as recited in claim 4, wherein said room-temperature-curable material has a viscosity at least approximately ten times the viscosity of said first material and said second material.

7. The device as recited in claim 1, wherein said first portion is made by molding said first portion of a silicone material.

8. The device as recited in claim 1, wherein said first portion is made by a process comprising the steps of:
   molding said gum portion of a first material;
   molding said tooth portion of a second material; and
   bonding said tooth portion to said gum portion.

9. The device as recited in claim 1, wherein said first material, said second material, and said room-temperature-curable material are selected from the group consisting of approximately 1:1 ratio curing silicone materials.

10. A method for making a cosmetic dental device, said method comprising the steps of:
    molding a gum portion of a first material, said gum portion having an outer surface shaped to resemble gum;
    molding a tooth portion of a second material, said tooth portion having an outer surface shaped to resemble a plurality of front teeth;
    attaching said tooth portion to said gum portion to make a shell;
    coloring said tooth portion to resemble natural teeth; and
    coloring said gum portion to resemble natural gum, said tooth portion and said gum portion being made of somewhat flexible materials so that said device is capable of being fitted to an individual user by applying a quantity of a room-temperature-curable material to an inner surface of said shell, positioning said shell so that said material engages at least some of the front teeth of a user, pressing said shell with said material against said front teeth until said material cures, removing said shell with said cured material from said front teeth, and trimming excess cured material from said shell.

11. The method as recited in claim 10, wherein said making step further comprises molding said shell as a single unit.

12. The method as recited in claim 10, wherein said shell and said room-temperature-curable material are medical grade or food grade silicone materials.

13. The method as recited in claim 10, wherein said room-temperature-curable material has a greater viscosity and a greater elongation than said shell.

14. The method as recited in claim 10, wherein said tooth portion has a hardness of 40–50 Shore A, said gum portion has a hardness of 20–40 Shore A, and said room-temperature-curable material has a hardness of 30–40 Shore A.

15. The method as recited in claim 10, wherein said first material, said second material, and said room-temperature-curable material are selected from the group consisting of approximately 1:1 ratio curing silicone materials.

16. A kit for making a cosmetic dental device for a user, said kit comprising:
    a first portion having an outer surface shaped to resemble an assemblage of front teeth, said first portion made of a nontoxic, nonirritating, somewhat flexible material, said first portion including a tooth portion made of a first material and a gum portion made of a second material;
    a second portion adapted for attachment to an inner surface of said first portion, said second portion made of a room-temperature-curable material so that said device can be fitted to said user by applying a quantity of said room-temperature-curable material to an inner surface of said shell, positioning said shell so that said room-temperature-curable material engages at least some of the front teeth of said user, pressing said shell with said room-temperature-curable material against said front teeth until said room-temperature-curable material cures, and removing said shell with said cured material from said front teeth, said first material being harder than said second material and said room-temperature curable material;
    instructions for fitting said device to said user; and
    a container for holding said first portion, said second portion, and said instructions.

17. The kit as recited in claim 16, wherein said first material, said second material, and said room-temperature-curable material are medical grade or food grade materials selected from the group consisting of approximately 1:1 ratio curing silicone materials.

18. The kit as recited in claim 16, wherein said first material has a viscosity of approximately 50,000–80,000 CPS at 72° F., wherein said second material has a viscosity of approximately 40,000–60,000 CPS at 72° F., and wherein said room-temperature-curable material has a viscosity of approximately 400,000–600,000 CPS at 72° F.

19. The kit as recited in claim 16, wherein said first material and said second material have elongations of at least approximately equal to 150%, and wherein said room-temperature-curable material has an elongation of at least approximately equal to 200%.

20. The kit as recited in claim 16, wherein said first material has a hardness of 40–50 Shore A and a viscosity of approximately 50,000–80,000 at 72° F., wherein said second material has a hardness of 20–40 Shore A and a viscosity of approximately 40,000–60,000 CPS at 72° F., and wherein said third material has a hardness of 30–40 Shore A and a viscosity of approximately 400,000–600,000 CPS at 72° F.

* * * * *